(12) United States Patent
Riekkinen et al.

(10) Patent No.: US 7,098,035 B2
(45) Date of Patent: Aug. 29, 2006

(54) MULTICELL CUVETTE PACKAGE, METHOD OF LOADING MULTICELL CUVETTES INTO A MEASUREMENT INSTRUMENT AND A DISPENSING DEVICE FOR LOADING CUVETTES

(75) Inventors: Jari-Pekka Riekkinen, Espoo (FI); Jukka Saukkonen, Espoo (FI)

(73) Assignee: Thermo Electron Oy, Vantaa (FI)

( * ) Notice: Subject to any disclaimer, the term of this patent is extended or adjusted under 35 U.S.C. 154(b) by 1031 days.

(21) Appl. No.: 09/988,046

(22) Filed: Nov. 16, 2001

(65) Prior Publication Data

US 2002/0027093 A1    Mar. 7, 2002

Related U.S. Application Data

(62) Division of application No. 08/966,708, filed on Nov. 10, 1997, now Pat. No. 6,328,164.

(30) Foreign Application Priority Data

Nov. 14, 1996    (FI) ...................................... 964556

(51) Int. Cl.
*B65D 69/00*    (2006.01)

(52) U.S. Cl. ..................... 436/43; 206/569; 206/460; 206/813

(58) Field of Classification Search ............... 436/43; 206/569, 460, 813
See application file for complete search history.

(56) References Cited

U.S. PATENT DOCUMENTS

| 3,759,374 A | 9/1973 | Helger et al. |
| 4,636,477 A | 1/1987 | Ronka et al. |
| 4,690,900 A | 9/1987 | Kimmo et al. |
| 5,048,957 A | 9/1991 | Berthold et al. |
| 5,055,262 A | 10/1991 | Sakagami |
| 5,251,778 A | 10/1993 | Eggl |

FOREIGN PATENT DOCUMENTS

| DE | 2711853 A1 | 9/1978 |
| DE | 3738375 A1 | 5/1989 |
| WO | 94/00362 A | 1/1994 |

*Primary Examiner*—Monique T. Cole
(74) *Attorney, Agent, or Firm*—Birch, Stewart, Kolasch & Birch, LLP.

(57) ABSTRACT

A cuvette package for loading multicell cuvettes from the package into measurement instruments having their cuvette loading accessories designed to accept known packages. On top of a row of multicell cuvettes is attached a detachable bonding strip having a width smaller than that of the width of the row of multicell cuvettes. The bonding strip serving to keep the row of cuvettes together during transport and being easily detachable when the cuvettes are being loaded into the instrument. The multicell cuvettes are loaded into the instrument from the dispensing device which supports the cuvette in place and has its top surface provided with an opening permitting the removal of the strip by pulling off from the supported multicell cuvette package.

4 Claims, 4 Drawing Sheets

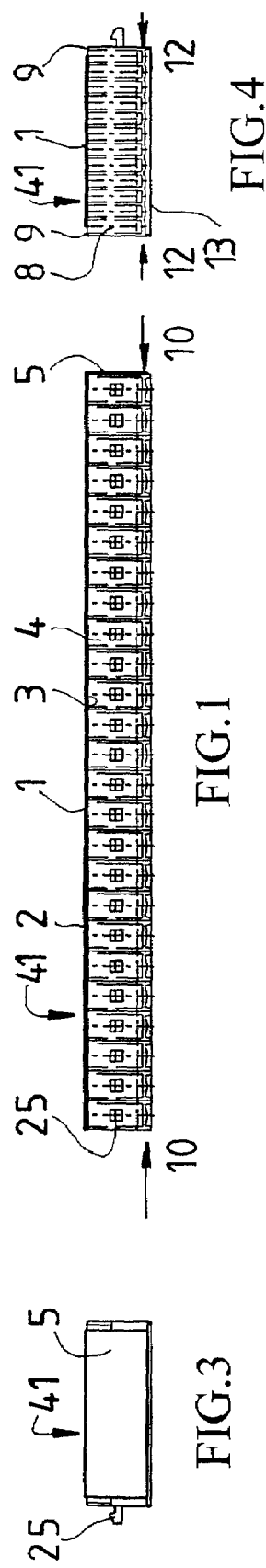

MULTICELL CUVETTE PACKAGE, METHOD OF LOADING MULTICELL CUVETTES INTO A MEASUREMENT INSTRUMENT AND A DISPENSING DEVICE FOR LOADING CUVETTES

This application is a divisional of application Ser. No. 08/966,708, filed on Nov. 10, 1997 now U.S. Pat. No. 6,328,164 the entire contents of which are hereby incorporated by reference and for which priority is claimed under 35 U.S.C. § 120; and this application claims priority of application No. 964556 filed in Finland on Nov. 14, 1996 under 35 U.S.C. § 119.

BACKGROUND OF THE INVENTION

1. Field of the Invention

The present invention relates to a cuvette package, a method of loading multicell cuvettes packaged in such a package into a measurement instrument and a dispensing device for loading multicell cuvettes from said package according to the invention into measurement instruments having their cuvette dispensing means designed for packages that have been used earlier.

2. Description of the Related Art

For the assay of different liquids, analytic laboratories employ automatic analyzers in which the liquids to be assayed are placed in reaction vessels, designed to perform simultaneously as cuvettes of high optical quality. Generally, a row of reaction vessels or single-cell cuvettes may be combined into a multicell module of reaction vessels, separated from each other by a vertical wall and cast into a single-piece row. Herein, the reaction vessels are adapted side-by-side into an integral module with a common wall separating any two adjacent vessels and the long vertical sides of the multicell cuvettes made straight so that the multicell cuvettes in turn can be placed side-by-side into a contiguous row in which the long sides of the cuvettes are tightly adjacent to each other. Thus, the cuvettes can be stored in a rectangular container during transport and other handling. Such a multicell cuvette design is disclosed in U.S. Pat. No. 1,690,900. Cuvettes of the above-described type are easy to handle and give reliable measurement results.

In use, cuvettes must be kept free from dust, scratches and breakage so that the radiation passed in the analyzing instrument via the transmissive window surfaces of the reaction vessels would give reliable assay results. Hence, cuvettes must be treated with great care immediately after their manufacture in the subsequent packaging, storage, transport and measurement steps.

In the practical use of such cuvettes, a need has arisen for such a packaging method of cuvettes that can keep the cuvettes absolutely free from dust, scratches and fingerprint stains. While the packaging step ensuing the injection-molding of the cuvettes can be performed fully controlled by automation methods and means, impact blows and human mishandling of the cuvette packages themselves during the loading of the cuvettes into the analyzing instrument have caused problems. To minimize such drawbacks, a cuvette packaging method has been developed in which the cuvettes are packaged into a row placed in a covered box with a removable cover. The mouth part of the package is shaped to fit into the cuvette intake port of the instrument, and the push lid of the package is provided with a pusher element for loading the cuvettes into instrument. When the package is attached to the cuvette intake port of the instrument, the cuvettes are transferred into the instrument by way of pushing the row of multicell cuvettes from behind with the help of the detachable push lid of the package, said lid incorporating a separate pusher element, which forms the other end of the package when the lid is still attached to the package. The benefits of this packaging method include dust-free handling, freedom from fingerprint contamination on the optical window areas of the cuvette or scratches of the same due to manual handling. Such a loading procedure and package is described in U.S. Pat. No. 4,636,477.

Such a box package has, however, some drawbacks which deteriorate its handling properties and increase packaging costs. The manufacture of the packaging box is costly in regard to the cost of cuvettes, whereby the unit price of assays will be increased by the expensive package. The discarded packages leave a great amount of plastic scrap to be transported to a dump or plastic materials recycling site. As the consumption of cuvettes in many laboratories has a high volume and the material of the packaging box may be different from the other plastic scrap resulting from the operation of the laboratory, this conventional arrangement is inferior in terms of recycling. Furthermore, the sorting and storage of cuvette packages in the laboratory spaces is clumsy. Since cuvettes are disposables and thus should not be recycled but as material, the cuvette package should contain the absolute minimum of material and the packaging materials should be easy to collect and recycle. While cuvettes in principle could be washed and reused, their optical window surfaces are extremely sensitive to contamination and mechanical damage. Therefore, cuvette manufacturers advise against reuse of cuvettes, because the risk of erroneous measurement results due to damaged/soiled cuvettes is high in the reuse of cuvettes.

Due to lower cost and material minimization, the cuvette packaging box must be made from thin material, whereby its rigidity is impaired. Resultingly, the box is readily warped and distorted as well as clumsy to use; the box and the cuvettes therein tilt easily, the cuvettes topple during their loading into the instrument and the box mouth cannot be held positively mounted on the cuvette intake port of the instrument. When fallen or tilted cuvettes are guided or erected manually, they are easily damaged by fingerprints or even scratches, which may cause erroneous measurement results. One problem hampering conventional packages is that the intake capacity of cuvette loading bays varies between different instrument makes, whereby also a varying number of excess cuvettes will always remain in the cuvette packages, and resultingly, the next batch of cuvettes must be loaded from two boxes in succession, whereby the number of incorrectly loaded cuvettes obviously will be higher.

U.S. Pat. No. 3,759,374 (Helger et al) discloses a cuvette package wherein the individual cuvettes are bonded together by a film or foil attached to the openings of the cuvettes. The foil is provided with severing lines for separating the cuvettes from each other and the foil can be removed simultaneously. The drawback of this method is that each cuvette has to be separated from the package by hand and the surface of the cuvettes may be thus contaminated. Also separation of the cuvettes by hand from the package requires al lot of manual work and is very slow. Thus this package provides a lucrative method for sealing the cuvettes and forming a transport package but the package and cuvettes are cumbersome to handle in laboratories.

SUMMARY OF THE INVENTION

It is an object of the present invention to provide a cuvette package and a compatible method of loading multicell cuvettes from such a package into an instrument, said package and method offering essentially reduced material consumption in the manufacture of the package, a lower rate of errors in cuvette loading and more effective elimination of inadvertent damage to cuvettes.

It is a further object of the invention to provide a dispensing device for loading multicell cuvettes stored in a package according to the invention into instruments intended to accept loading from cuvette box package.

The goal of the invention is achieved by attaching on top of a row of multicell cuvettes such a detachable bonding strip of a width smaller than that of the width of the multicell cuvettes, said bonding strip serving to keep the row of cuvettes together during transport and to be easily detachable when the cuvettes are being loaded into the instrument.

According to the invention, the cuvettes are bonded into a package with the help of a single strip of self-adhesive tape or similar band whose underside can be attached to the tops of cuvettes placed in rows. Besides the cuvettes, the package thereby contains no other parts or materials except the easily disposable strip of self-adhesive tape. Resultingly, the amount of packaging material to be discarded remains minimal. The strip protects the reaction spaces of the cuvettes very efficiently from dust and debris even up to the most distal cuvettes in the row. The rear end of the strip is folded over the optical window area of the last cuvette in the row so as to form a handling shield thus permitting manual pushing of the row of cuvettes from the rear side of the row, whereby the optical window surfaces of the last multicell cuvette in the row need not be touched by fingers at any moment. The number of cuvettes in a package and the dimensions of the cuvette dispensing device of the measurement instrument are standardized, whereby each package contains a row of 25 multicell cuvettes, which can be loaded as a batch into the instrument. This arrangement avoids the storing of half-empty packages.

The novel package according to the invention is cheaper than a conventional box package and produces less plastic scrap. The cuvettes are easier to load from the package according to the invention into a measurement instrument of suitably designed construction, and when the loading operation is performed using the full cuvette batch of the novel package, there is no need nor opportunity offered for handling cuvettes individually. This arrangement assures maximum hygienic and optical cleanliness of cuvettes and prevents mechanical damage thereto. As contamination and marring of cuvettes can essentially impair the reliability of measurement results, cleanliness and intact condition of cuvettes is crucially important for reliable function of measurement instruments.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the following, the invention will be examined in greater detail with the help of the appended drawings which are given by way of illustration only, and thus are not limitative of the present invention, and wherein:

BRIEF DESCRIPTION OF THE DRAWINGS

FIG. 1 shows a side view of an embodiment of the cuvette package according to the invention;

FIG. 2 shows a top view of an embodiment of the cuvette package according to the invention;

FIG. 3 shows an embodiment of the cuvette package according to the invention viewed from the end of the package to be attached to the measurement instrument;

FIG. 4 shows an embodiment of the cuvette package according to the invention viewed from the end of the package protected by the bonding strip;

DETAILED DESCRIPTION OF THE INVENTION

Figure 5:
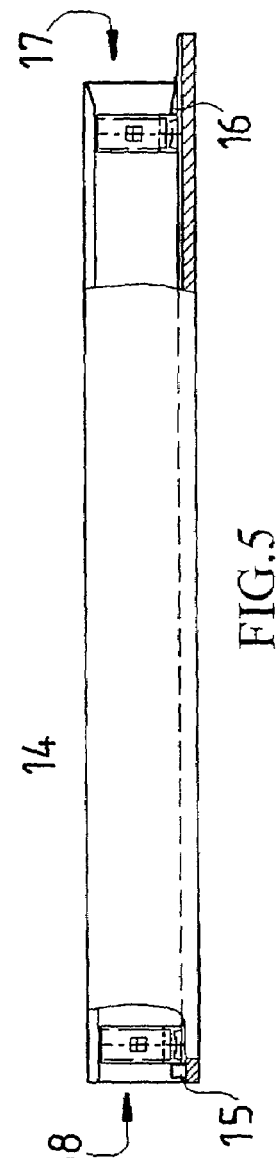
FIG. 5 shows a side view of an embodiment of the cuvette dispensing device with the cuvette package placed therein.

Referring to FIG. 1, therein is shown a cuvette package 41 according to the invention. The package is comprised of a plurality of conventional multicell cuvettes 4 of multiple reaction vessels, placed in a row, and of a bonding strip 1 serving to keep the multicell cuvettes together in the row. Each multicell cuvette 4 has a hook member 25, from which the multicell cuvette 4 can be grasped for transport within the measurement instrument. The bonding strip 1 is attached to the multicell cuvettes by means an adhesive coating 3 placed on the underside of the strip, whereby the strip adheres to the top of the multicell cuvettes at the area surrounding the mouths of the reaction vessels. The strip 1 may be made from, e.g., self-adhesive polypropylene tape having its adhering surface covered with an acryl-based adhesive of good weather and low/high temperature resistance. The bonding strength must be so high that, on one hand, the package can be handled by lifting or bending, for instance, and, on the other hand, the strip can be removed by pulling with a moderate force. Furthermore, the adhesive coating 3 must be non-staining and of a type that leaves no excessive residues of the adhesive on the rim surfaces of the reaction vessels when removed therefrom.

The adhesive, which may be formulated from, e.g., an acryl dispersion, is selected to have suitable adhesion and removal force properties. The cold/hot temperature resistance of the adhesive must be sufficiently good to avoid inadvertent detachment of the bonding strip during storage. Obviously, the adherence strength of the adhesive need to be compatible with the available bonding area, whereby the bonding strength between the bonding strip 1 and the multicell cuvettes 4 can be varied by modifying the surface area used for bonding. The adhesive can be applied over a narrow area at the strip edges, or in the strip center or over any other suitable area, or obviously, even over the entire width of the strip.

The leading end of the bonding strip 1 is formed into a pull tab 2 which is folded over the top of the row of multicell cuvettes for the duration of transport and storage. The pull tab 2 is made sufficiently long for a convenient grasp with fingers and it is left free from the adhesive coating. The trailing end of the bonding strip 1 is formed into a skirt tab 5, bent over the optical window area 8 of the last cuvette in the row, whereby the skirt tab makes it possible to push the row of multicell cuvettes from the rear side of the row without contaminating the optical area 8 of the last cuvette in the row. The length of the skirt tab 5 is selected so that overlapping length of the tab is slightly shorter than the height of the cuvette, yet sufficiently long to cover the optical area 8. Thus, the last cuvette in the row can be supported by its lower edge without any interference by the skirt tab 5 which gives protection to the optical area 8. The underside of the pull tab 2 and the trailing end skirt tab 5 of the bonding strip are left free from the adhesive coating.

The bonding strip 1 is made narrower than the cross-package length of the multicell cuvette 4, whereby a gap 7 remains between the outer edges of the strip 1 and the ends of the multicell cuvette 4. When the package is being unloaded, the row of multicell cuvettes can be supported from above at the edge 9 of the row of the multicell cuvettes. The bonding strip 1 covers almost perfectly the mouths of the reaction vessel spaces 6 formed in the multicell cuvettes, thus protecting the cuvettes from gathering dust. The mouths of the most peripherally situated reaction vessels may be left marginally covered at the edges. When the cuvettes are being loaded in the measurement instrument, the bonding strip 1 can be removed—at the same time relieving the cuvettes from the package—by supporting the package simultaneously at its front edge 11, rear edge 10, on top at the free edges 9 and from the direction of the package bottom 13 and sides 12. When the package is supported in the above-described manner, it can be unloaded by pulling the bonding strip off from the top surface of the multicell cuvettes 4, whereby the cuvettes are detached from the adhesive coating 2 of the bonding strip.

The bonding strip 1 can be made from a variety of different materials, and respectively, its detachable bonding can be implemented using a plurality of different methods. Most advantageously, the strip is made from an elastic and flexible material such a polypropylene or reinforced paper. Preferably, the strip is made maximally wide, whereby it will cover the reaction vessels during transport. Obviously, the strip may be made very narrow if the protection of the cuvettes is simultaneously secured by placing the cuvette packages into larger, dust-proof transport containers. When a wide bonding strip is used, the adhesive can be applied to selected areas of the strip only, e.g., as narrow stripes of adhesive at the edges of the strip. In the case that the adhesive is placed on narrow areas only, the adhesive can have a high tacking power if the required easy detachability is simultaneously assured by making the area of adherence sufficiently small. When the bonding strip is adhered using ultrasonic welding or heat-sealing, its attachment can be advantageously accomplished by means of spot-like bonding surfaces, whereby the proper bonding strength may be controlled by altering the number of the bonding spots. The strip may be made from a material of higher stiffness, whereby also the package will become rigid.

Figure 7:
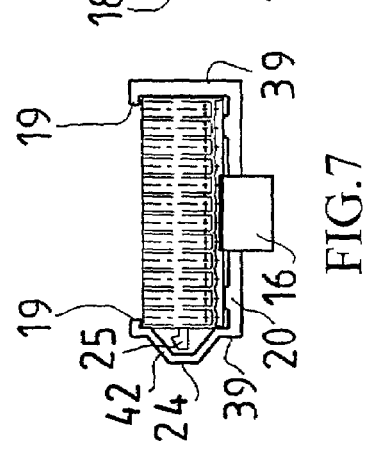
FIG. 7 shows an embodiment of the cuvette dispensing device with the cuvette package placed therein as viewed from the direction of the cuvette intake port of the measurement instrument.
Figure 6:
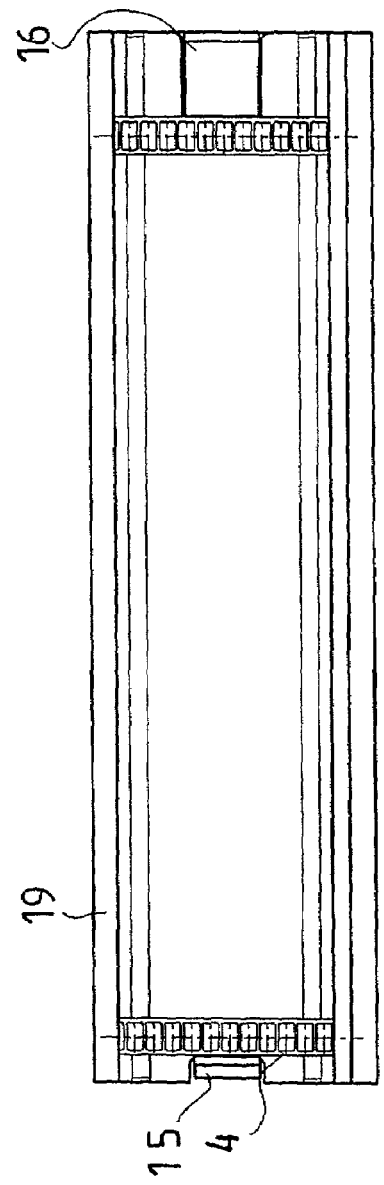
FIG. 6 shows a top view of an embodiment of the cuvette dispensing device with the cuvette package placed therein.

In FIGS. 5–7 is shown a dispensing device particularly suited to serve as an automatic dispensing device for loading multicell cuvettes into measurement instruments. Such a cuvette dispensing device has a frame 14 containing a gutter-like space suited to accommodate the cuvette package 41. The frame is made from an aluminum continuous section. The sides of the package space are formed by upright walls 39 terminating at their upper edges with lips 19 pointed toward the center line of the dispensing device. Both ends of the dispensing device have stops 15 and 16 serving to locate the front and rear ends 11, 10 of the cuvette package in place. One internal wall 39 of the package space is provided with an elongated groove-like recess 24 dimensioned to accommodate the hooked end 25 of the multicell cuvettes 4. The bottom of the package space has elevated guide rails 20 on which the multicell cuvettes can slide without damage. One or more of these cuvette dispensing devices may be used as an automatic loading accessory when connected to measurement instruments. If a number of cuvette dispensing devices are used in combination, they can be arranged in different ways movable on guides so as to be sequentially transferable to coincide with the cuvette intake port of the instrument, or alternatively, the dispensing devices can be adapted to form a revolver magazine.

From the package according to the invention, the cuvettes are loaded into the instrument by virtue of the above-described dispensing device in the following manner.

The cuvette package 41 is placed in the dispensing device by pushing the package into the package space via infeed end 17 of the device, whereby the trailing end skirt tab 5 provides protection for the optical window surface of the cuvette against fingerprints. A stop 16 at the infeed end 17 is simultaneously pushed receding downward so as to permit free passage of the cuvette row, while a stop 15 at the outfeed end 18 of the device counters the passage of the package stopping it in place, whereby the infeed end stop 16 can rise up. The lips 19 of the device frame 14 give support to the cuvettes from above, while the walls 39 support the package from the sides and the guides 20 of the frame bottom provide support from below. Thus, the cuvettes are supported from all sides into a fully stabilized position. The strip joining the cuvettes remains in the free area between the lips 19, wherefrom it can be removed by pulling from the pull tab 2 of the strip 1. Next, the cuvettes can be fed forward by opening the outfeed end stop 15 and pushing the last cuvette from the side closer to the infeed end 17. Advantageously, the cuvettes are pushed with the help of a separate, automatic pusher means, whereby the only task remaining for the instrument user to carry out is the insertion of a new cuvette package into the cuvette dispensing device after the previous cuvette batch is exhausted. The exhaustion of cuvettes can be signaled by a visual, audible or other suitable indicator means.

Figure 8:
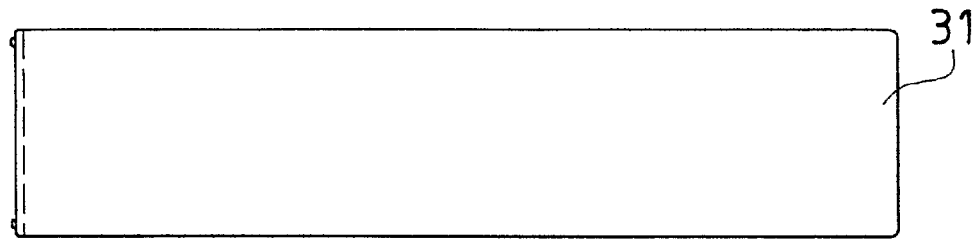
FIG. 8 shows a top view of the dust protection cover of a separate cuvette caddy box.
Figure 9:
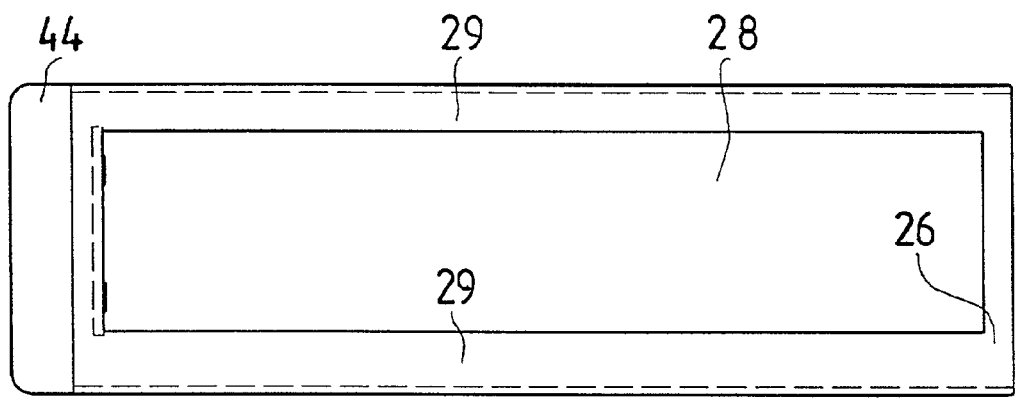
FIG. 9 shows a top view of the discharge end cover of the separate cuvette caddy box.
Figure 10:
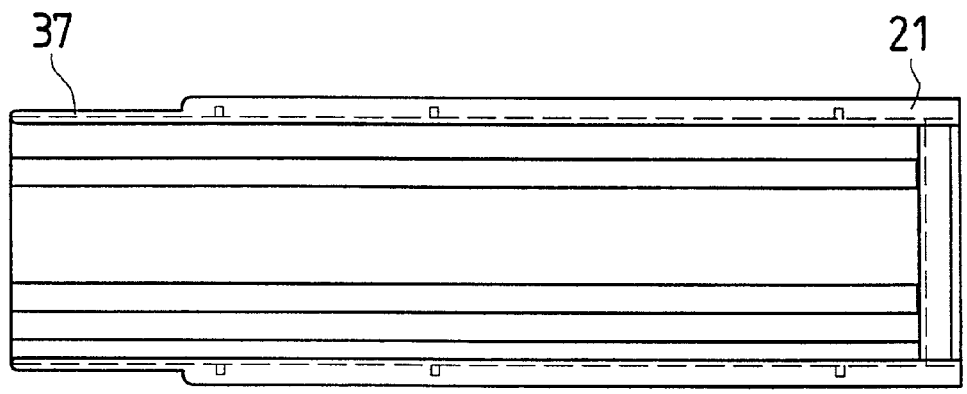
FIG. 10 shows a top view of the separate cuvette caddy box.
Figure 14:
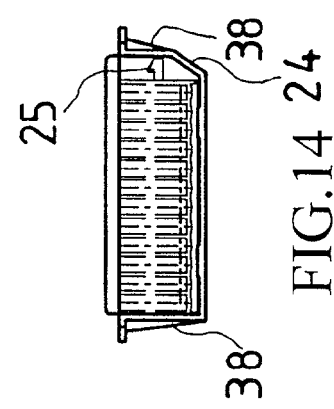
FIG. 14 shows the separate cuvette caddy box with the cuvettes therein as viewed from the direction of the cuvette intake port of the measurement instrument.
Figure 11:
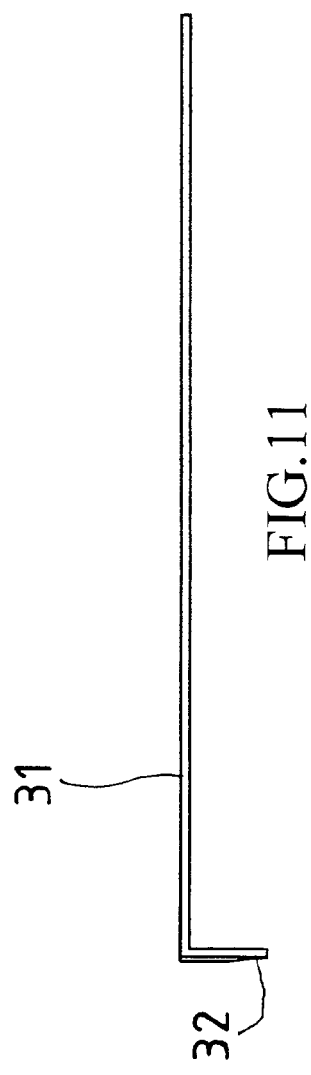
FIG. 11 shows a side view of the dust protection cover of the separate cuvette caddy box.
Figure 12:
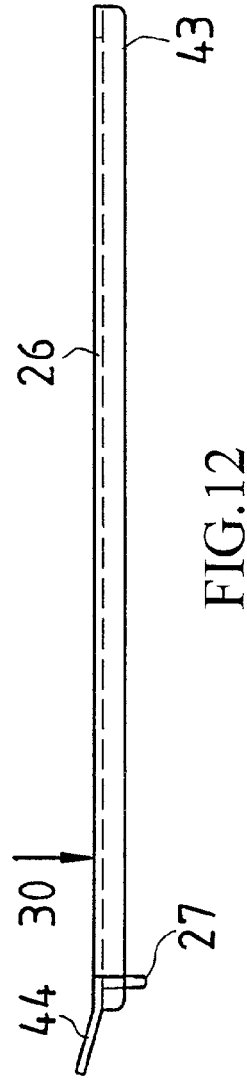
FIG. 12 shows a side view of the discharge end cover of the separate cuvette caddy box.
Figure 13:
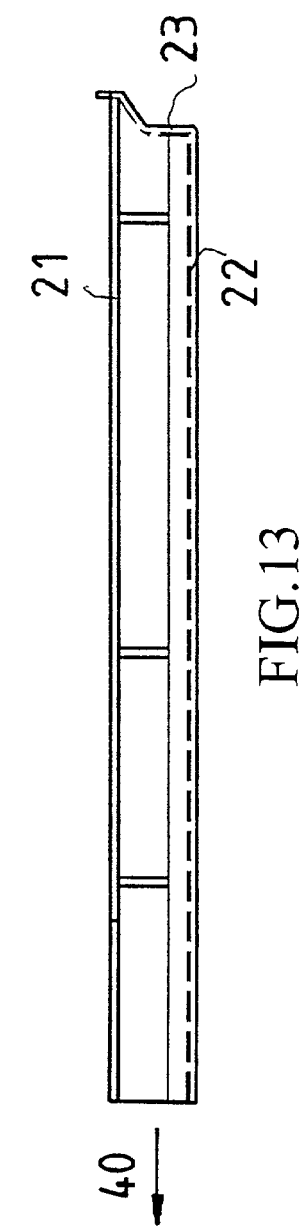
FIG. 13 shows a side view of the separate cuvette caddy box.

In FIGS. 8–14 is illustrated a device suited for the cuvette package unloading and manual infeed of the multicell cuvettes. FIG. 8 shows a top view of a pusher element serving for manual pushing of cuvettes; FIG. 11 shows the same element in a side view. In FIG. 9 is shown a top view of the cover 26 via which the bonding strip of the cuvette package can be removed. FIG. 12 shows the same cover 26 in a side view. In FIG. 10 is shown a separate cuvette caddy box 21 into which the cuvettes are placed during the package unloading step. In FIG. 13 the same caddy box is shown in a side view and in FIG. 14 in a front view.

The pusher element comprises a push lid 31 and a push edge 32. The push lid 31 is dimensioned so that it covers the opening of the dispensing device cover 26, whereby the lid acts as a dust cover of the dispensing device. The push edge 32 is dimensioned so as to permit the movement of the push lid in the cuvette storage space of the caddy box 21. The dispensing device cover 26 has narrow lips 43 dimensioned to mate with the edges of the internal walls of the caddy box 21. Additionally, the cover 26 is provided with an opening 28 bordered by edges 29. The front edge of the cover includes a backing lip 27 and a lift edge 44. The opening 28 of the dispensing device cover is dimensioned wider than the bonding strip 1 joining the row of cuvettes, but narrower than the cross-package width of the row of multicell cuvettes, whereby the multicell cuvettes placed in the caddy box 21 can be supported from above by means of the dispensing device cover 26. The caddy box 21 itself comprises a bottom 22, side walls 24 and 38 as well as a rear end wall 23. One side wall 38 is upright straight, while the other side wall 24 is made slanted at its edge joining with the bottom 22, whereby the upright straight side of the cuvette row can be placed abutting the straight wall 38 and the hooked end 25 of each multicell cuvette in the row is situated facing the slanted wall 24, where the properly dimensioned slanted side of the wall provides extra space to accommodate the hooked end 25 of the multicell cuvettes. The mouth part 37 of the caddy box 21 is dimensioned to match the dimensions of the cuvette intake port of the instrument.

When the cuvettes are loaded into the instrument by means of the above-described device, the cuvette package is first placed into the caddy box 21. The bottom 22 of the caddy box supports the cuvettes from below, the rear end wall 23 from behind the last cuvette in the row and the walls 38 and 24 from the sides. Herein it must be noted that the slanted wall 24 on one side of the caddy box 21 inhibits the cuvettes from being placed in the caddy box in any other way but with the hooked end 25 facing the slanted wall. Next, the caddy box is covered with the dispensing device cover 26. The backing lip 27 of the cover supports the cuvettes from the front side. The opening 28 on the cover top is made wider than the cross-package width of the bonding strip joining the cuvette tops, yet narrower than the cross-package length of the multicell cuvettes. Thus, the edges 29 of the opening can support the cuvettes from above. For the duration of the strip removal step, the cover must be locked to the caddy box 21, or alternatively, compressed against the caddy box, e.g., manually in the direction of arrow 30 in the diagram. Thus, the cuvettes will be clamped in place and the strip can be safely removed via the opening 28 by pulling from the pull tab 2. After the removal of the bonding strip 1, the cuvettes can be loaded into the instrument by elevating the dispensing device cover 26 and actuating the push lid 31. The push edge 32 at the front end of the push lid is inserted in the interior of the rear end 23 of the caddy box, behind the last multicell cuvette in the row, and the cuvettes are transferred out from the box into the measurement instrument in the direction of arrow 40 in the diagram. The infeed end 37 of the caddy box is designed to be compatible with the cuvette-handling mechanisms of the instrument. Also the push lid 31 is dimensioned so that it can cooperate with said mechanisms of the instrument. The push lid 31 can be used as a dust cover by placing it over the opening 28 of the dispensing device cover so that the lid covers the entire opening and has the push edge 32 at its front end located pointing outward from the top of the caddy box. Positive locking of the different elements to each other can be assured by providing the element with conventional clamping means.

In addition to those described above, the invention may have alternative embodiments.

As mentioned above, the bonding strip joining the row of multicell cuvettes may be made from different types of materials and with varying dimensions. Furthermore, the bonding strip may be adhered to the cuvettes using a plurality of different methods. The strip can be provided with printed information such as operating instructions, manufacturer's name and labeling as well as other information concerning the use and recycling of the package. The design of cuvette dispensing devices may be varied widely as to their external form, provided that the device in all of its embodiments provides sufficient space to accommodate a row of cuvettes and has means for supporting the cuvettes from above during the strip removal step. Alternatively, the cuvettes can be loaded using a conventional cuvette dispensing box if the loading system is complemented with a dispensing device cover of the kind shown in FIG. 12 to facilitate the removal of the bonding strip, by means of which cover the cuvettes can be supported in the caddy box during the strip removal step. The caddy box and the cover can be connected with each other by a hinge or other suitable means. Furthermore, the dispensing device cover and the push lid can be designed into an integral entity, because after the strip is removed, the cuvettes need no more any support from the dispensing device cover. However, then the cover must be provided with a removable or hinged lid via which the strip can be removed. The cuvette caddy box or cuvette loading device need not be a box with solid walls, but instead, a partially open structure such as one having walls of a mesh or lattice structure can be used. In addition to different metals, the frame of the cuvette caddy box or cuvette dispensing device can be made from different types of polymers or composite materials, even prepared into continuous sections of varying shapes. While the number of cuvettes in the package may be varied, the use of standardized package size is obviously the most advantageous choice for both the instrument user and the cuvette supplier.

The invention claimed is:

1. A method of loading multicell cuvettes into a measurement instrument, in which method a cuvette package is placed in a device frame which has a space to accommodate said cuvette package and from which the multicell cuvettes of the cuvette package can be unloaded into said instrument, wherein:

supporting the cuvette package at least from its rear end at the last multicell cuvette in the row, from in front of the package, from the bottom side of the multicell cuvettes and, at the mouth level of the reaction vessels, along the edge area adjacent to the bonding strip which keeps the multicell cuvettes of the package together, and pulling the bonding strip keeping the cuvette package together off from the multicell cuvettes, whereby said cuvettes are separated from each other for loading into said instrument.

2. The method as defined in claim 1, wherein the cuvette package is supported at its edge by placing over the cuvette package a dispensing device cover having an opening with a width not smaller than the width of the bonding strip, via which opening it is possible to remove the bonding strip that keeps the package together.

3. The method as defined in claim 1, wherein the cuvette package is supported at its edge by means of lips formed to side walls of the device frame.

4. The method as defined in claim 2, wherein, after the bonding strip serving to keep the cuvette package together is removed, the dispensing device cover is removed from above the caddy box and the multicell cuvettes are loaded with the help of a separate pusher element into the measurement instrument.

* * * * *